US 6,575,980 B1

(12) United States Patent
Robie et al.

(10) Patent No.: US 6,575,980 B1
(45) Date of Patent: Jun. 10, 2003

(54) METHOD AND APPARATUS FOR FEMORAL RESECTION

(75) Inventors: Bruce Robie, New York, NY (US); Jordan Ryalls, New York, NY (US); Joseph Lipman, New York, NY (US); Albert H. Burstein, Longboat Key, FL (US); Thomas P. Sculco, New York, NY (US)

(73) Assignee: New York Society for the Ruptured and Crippled Maintaining the Hospital for Special Surgery, New York, NY (US)

( * ) Notice: Subject to any disclaimer, the term of this patent is extended or adjusted under 35 U.S.C. 154(b) by 0 days.

(21) Appl. No.: 09/362,599

(22) Filed: Jul. 28, 1999

Related U.S. Application Data (63) Continuation-in-part of application No. PCT/US98/01655, filed on Jan. 27, 1998.
(60) Provisional application No. 60/036,220, filed on Jan. 28, 1997.

(51) Int. Cl.⁷ ............................................. A61B 17/58
(52) U.S. Cl. ............................. 606/88; 606/82; 606/86; 606/88
(58) Field of Search ............................... 606/79, 86–88, 606/80, 82, 90

(56) References Cited

U.S. PATENT DOCUMENTS

| | | | |
|---|---|---|---|
| 2,794,253 A | 6/1957 | Fitzsimmons | |
| 4,424,035 A | 1/1984 | Hansen | |
| 5,098,436 A | 3/1992 | Ferrante et al. | |
| 5,258,032 A | 11/1993 | Bertin | |
| 5,454,816 A | * 10/1995 | Ashby | 606/88 |
| 5,458,645 A | 10/1995 | Bertin | |
| 5,474,559 A | 12/1995 | Bertin et al. | |
| 5,514,139 A | 5/1996 | Goldstein et al. | |
| 5,571,197 A | 11/1996 | Insall | |
| 5,601,563 A | 2/1997 | Burke et al. | |
| 5,649,929 A | * 7/1997 | Callaway | 606/88 |
| 5,665,090 A | 9/1997 | Rockwood et al. | |
| 5,688,282 A | * 11/1997 | Baron et al. | 606/87 |
| 5,702,460 A | 12/1997 | Carls et al. | |
| 5,716,361 A | 2/1998 | Masini | |
| 5,800,438 A | * 9/1998 | Tuke et al. | 606/90 |
| 5,830,216 A | * 11/1998 | Insall et al. | 606/87 |
| 5,860,981 A | * 1/1999 | Bertin et al. | 606/88 |
| 5,879,393 A | 3/1999 | Whiteside et al. | |
| 6,077,270 A | * 6/2000 | Katz | 606/88 |

FOREIGN PATENT DOCUMENTS

| | | |
|---|---|---|
| SU | 1600749 | 10/1990 |
| WO | WO 98/52499 | 11/1998 |

\* cited by examiner

*Primary Examiner*—Gary Jackson
(74) *Attorney, Agent, or Firm*—Darby & Darby (57) ABSTRACT

An instrument is provided for use in shaping a femur preparatory to implantation of a knee prosthesis. A gap checking device is fixed to the distal end of the patient's femur and referenced to the epicondyles of the femur. The gap checking device includes slots through which a cutting instrument can be passed to shape the femur so that it can receive the femoral component of the prosthesis. One of the slots enables the distal femoral cut to be made. The thickness of the gap checking device is selected so that the distance between the distal femoral cut and the distal surface of the gap checking device plus the thickness of a shim resting on the cut proximal tibia surface is equal to the combined thickness of the tibial and femoral components of the prosthesis. This enables balancing of the ligaments to be checked before the femoral cuts are made, but while the gap checking device is secured to the femur.

36 Claims, 13 Drawing Sheets

METHOD AND APPARATUS FOR FEMORAL RESECTION

CROSS-REFERENCE TO RELATED APPLICATIONS

This application claims priority pursuant to 35 U.S.C. 119 based upon U.S. Provisional Application Ser. No. 60/036,220 filed Jan. 28, 1997, the entire disclosure of which is incorporated herein by reference.

This application further is a continuation-in-part of International Application No. PCT/US98/01655 filed Jan. 27, 1998, the entire disclosure of which is also incorporated herein by reference.

BACKGROUND OF THE INVENTION

1. Field of the Invention

The present invention relates to an instrument and method for shaping a femur preparatory to implanting a knee prosthesis.

2. Description of Related Art

A total knee replacement or prosthesis, substitutes for a patient's arthritic or otherwise dysfunctional natural knee joint. The prosthesis offers the patient an alternative treatment for the chronic pain and discomfort often associated with such problems.

Burstein et al. U.S. Pat. No. 4,298,992 illustrates a popular total knee joint prosthesis known as the Insall-Burstein (I/B) knee. Such prostheses comprise a femoral component attached to the patient's femur, a tibial component attached to the patient's tibia, and a patellar component attached to the patient's patella. To use this prosthesis, it is necessary to shape by resection the patient's femur, tibia and patella. The tibia and patella are shaped by a flat cut. In the case of the I/B prosthesis, the femoral component requires five cuts about the periphery of the femur and three cuts in the intercondylar notch in the distal end of the femur. These cuts conform to complementary portions of the femoral component which engage the bone. It is important that these femoral cuts be made precisely and located so that the position of the femoral component and the tibial component will closely approximate the positions of their anatomical counterparts. Proper positioning of the femoral and tibial components is required to insure the patient's natural anatomic limb alignment and normal anatomical movement.

As part of the installation of a knee joint prosthesis, it is important to balance the ligaments crossing the joint. Balancing the ligaments means performing soft tissue releases, as necessary, so as to ensure that when the femur is lifted off of the tibia by a force directed along the long axis of the tibia, and the tibia is positioned in natural anatomic limb alignment, the tension in the medial and lateral ligamentous support is nearly equal. In order for the ligamentous tension to be nearly equal, the distance between the medial aspect of the femur and tibia, and the lateral aspect of the femur and tibia must be nearly equal when the tibia is in natural anatomic limb alignment. The distance between the femur and tibia should also be approximately equal throughout the range-of-motion of the tibia from full extension to approximately 90 degrees of flexion. The distance between the femur and tibia is commonly called "the gap", and the process of lifting the femur, and measuring the distance between the femur and tibia is commonly called "checking the gap". Heretofore, gap checking has been done after the femur has been shaped and only at full extension, and 90 degrees flexion. If proper balancing can not be achieved, then it may be necessary to reshape the femur, which is obviously undesirable, or to use a more constrained total knee design, thus limiting knee motion.

An object of the invention is to provide an instrument for use in shaping the distal surface of a femur preparatory to implantation of a knee prosthesis in which the gaps can be checked and adjusted prior to shaping the femur. This eliminates the need to recut the femur and reduces the time required for surgery. Moreover, since it is easier to check the gaps with the invention, it is likely that more surgeons will take the time to check the gaps and, therefore, the quality of the surgery will improve.

A further object of the invention is to provide a device for shaping the distal surface of a femur preparatory to implanting a knee prosthesis wherein all of the cuts required to shape the femur can be made using a single instrument.

Yet another object of the present invention, is the ability to check the gaps continuously throughout the range-of-motion of the knee, not just at full extension and 90 degrees flexion, as with conventional devices.

The most popular types of instruments used to shape the femur are intramedullary devices in which a cutting guide is positioned at the distal end of the femur relative to a rod which is driven into the intramedullary canal of the femur. Historically, surgeons have also used extramedullary alignment to orient the instruments to cut the distal femur. The present invention may be used with intramedullary or extramedullary alignment techniques.

SUMMARY OF THE INVENTION

The principal component of the knee instrument according to the invention comprises a gap checking device which includes a curved base adapted to engage the distal end of the patient's femur. A plurality of slots are defined in the gap checking device for guiding the cutting instrument used to shape the femur. The gap checking device can be referenced to the patient's femur using conventional intramedullary or extramedullary locator techniques.

The thickness of the gap checking device is such that the distance between the distal cut in the femur to the distal surface of the gap checking device plus the thickness of a shim corresponds in a predetermined way to the thickness of the femoral and tibial components of the prosthesis. Accordingly, the gaps can be checked with the gap checking device after placing the shim on the cut surface of the tibia. The shim also protects the cut surface of the tibia to prevent bone damage. After the knee has been properly balanced, bone cuts are made by passing a cutting instrument through the slots in the gap checking device. If necessary, a slot extender may be attached to the gap checking device to extend or increase the length of the slots.

BRIEF DESCRIPTION OF THE DRAWINGS

The foregoing and other features of the present invention will be more readily apparent from the following detailed description and drawings of illustrative embodiments of the invention wherein like reference numbers refer to similar elements throughout the several views and in which:

FIG. 9b is a bottom view of the femoral component and the 8-in-1 gap checking device of FIG. 9a;

DETAILED DESCRIPTION OF THE PREFERRED EMBODIMENTS

The instrumentation according to the invention includes a locating device, a gap checking device and a slot extender. A locating device is first used to properly position the gap checking device on the distal end of the femur. The surgeon uses the gap checking device to balance the ligaments of the patient's knee before any of the femoral cuts are made. Once properly positioned, a cutting instrument or blade is guided through slots in the gap checking device in order to make the appropriate cuts in the femur. Prior to making the cuts, the slot extender may be attached to the gap-checking device to extend the length of the slots.

Figure 1:
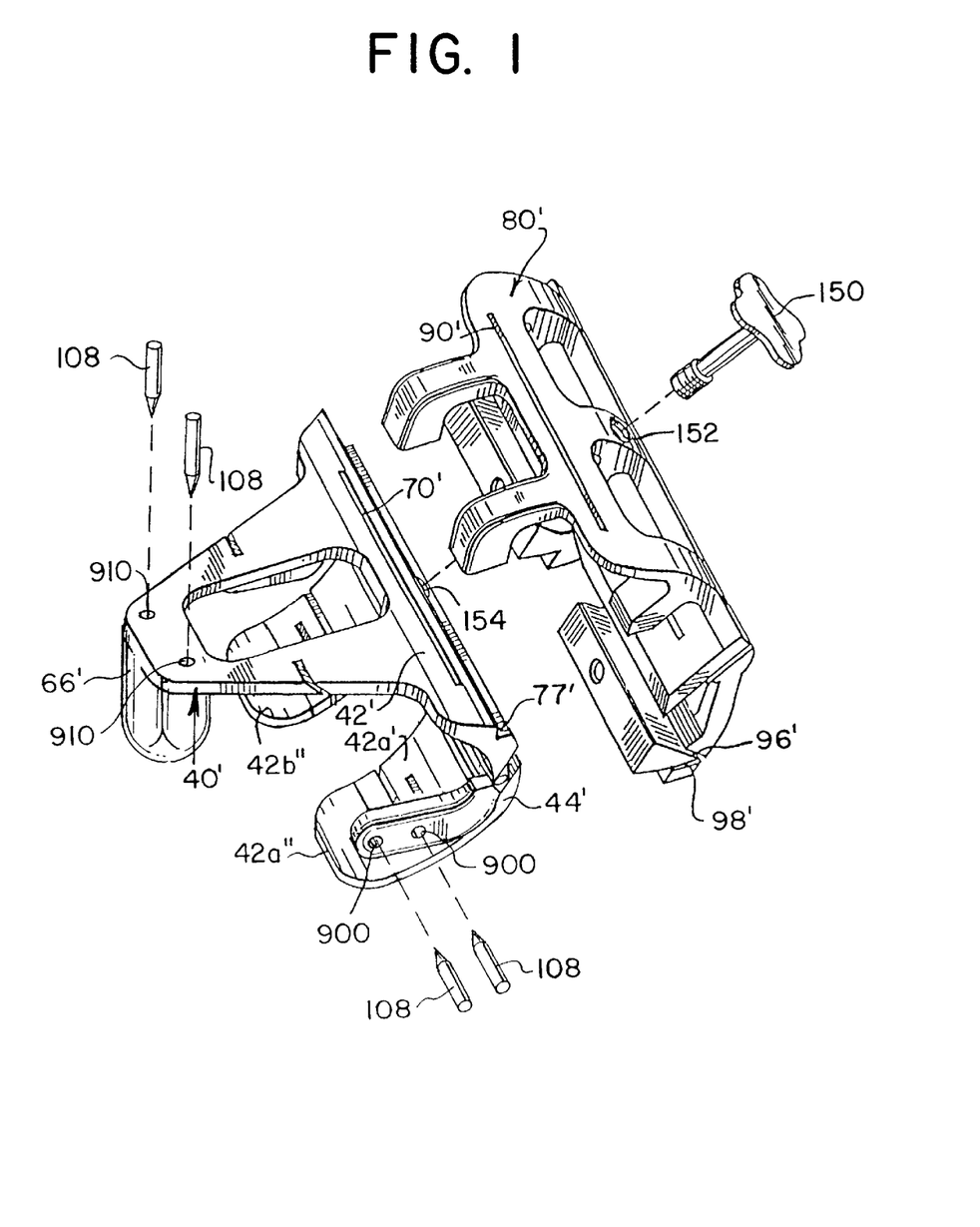
FIG. 1 is an exploded perspective view showing a 5-in-1 gap checking device and slot extender according to a first embodiment of the invention.

FIG. 1 is a first embodiment of a 5-in-1 gap checking device 40' and slot extender 80' in accordance with the present invention. Gap checking device 40' has a curved base 42' forming two bifurcated portions 42a' and 42b', which overlay the femoral condyles.

Figure 11:
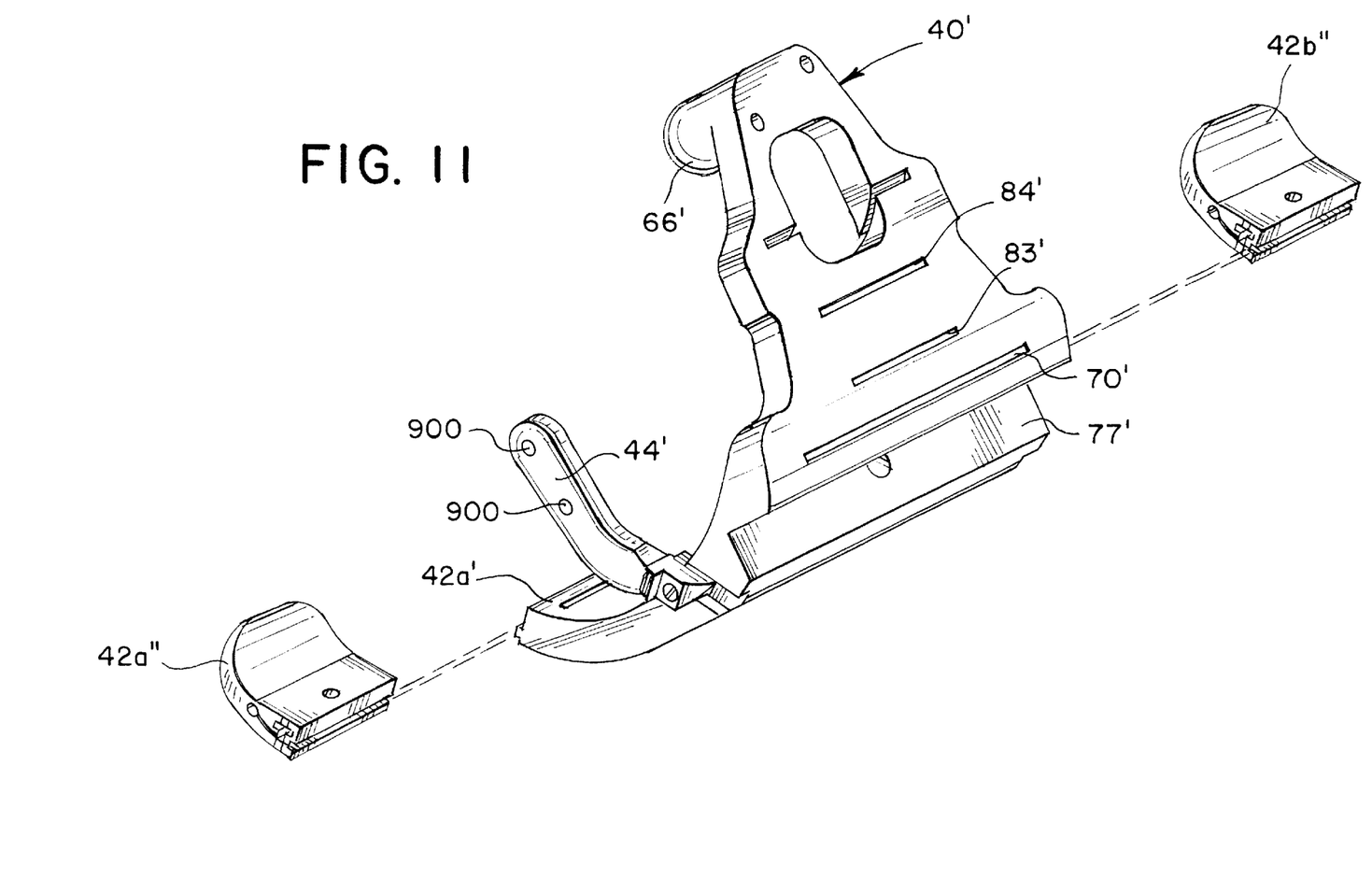
FIG. 11 is an exploded view of the 8-in-1 gap checking device with angle extender attachments in accordance with the present invention.

As shown in the exploded view in FIG. 11, angle extender attachments 42a", 42b" may be secured, for example, by dovetail or tongue-and-groove, to the free end of the portions 42a', 42b', respectively, to extend the base 42' around the femoral condyles in order to check the balance of the ligaments over a wider angular range, as explained in detail below. Outrigger arms 44' and 46' are immovably attached at one end to opposite sides of the base 42'. One or more apertures 900 are defined in the outrigger arms 44' and 46' through which pins 108 are inserted to secure the gap checking device 40' to the femur.

A ball tip 66' is mounted to one end of the curved base 42', which overlies the femur during the operation. Two bores 910 are defined through the ball tip 66' through which pins 108 are inserted to secure the gap checking device 40', when properly positioned, to the femur. As shown most clearly in FIGS. 3 and 5, the gap checking device 40' includes five slots 70', 72', 74', 76' and 78' which, as explained below, guide the blades used to shape the surface of the femur to receive the femoral component of the prosthesis.

Figure 10A:
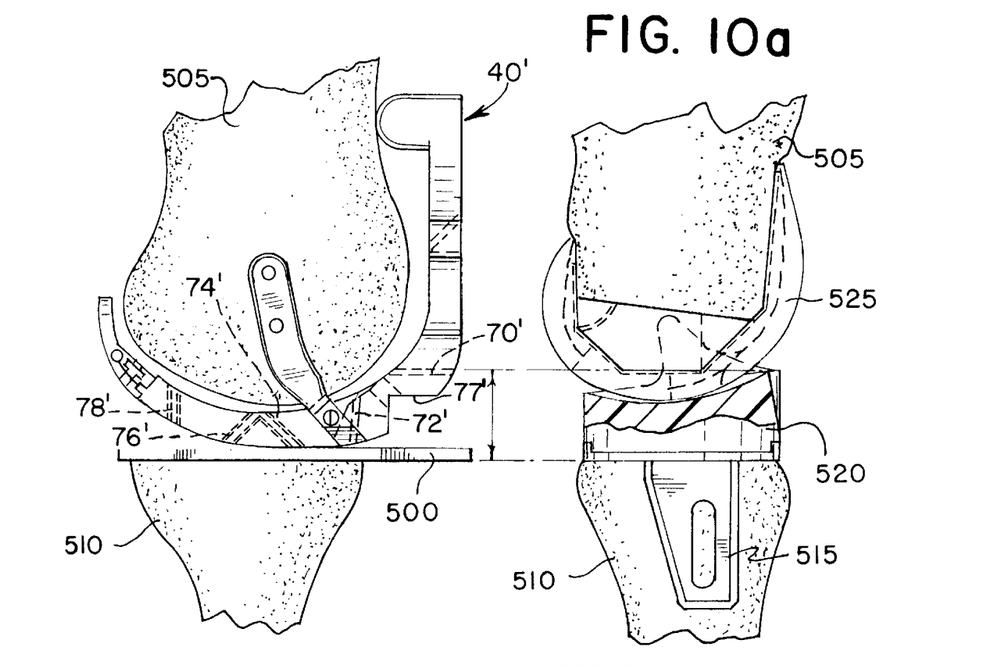
FIG. 10a is a side-by-side view of the 5-in-1 gap checking device in full extension before resection of the distal end of the femur and after resection with the knee prosthesis components.
Figure 10B:
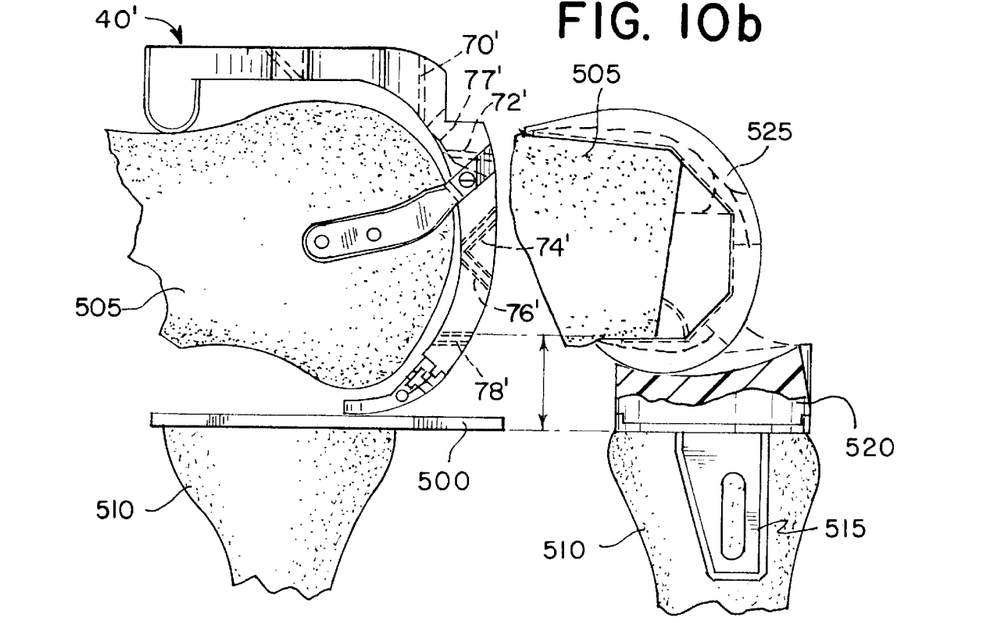
FIG. 10b is a side-by-side view of the 5-in-1 gap checking device in 90 degrees flexion before resection of the distal end of the femur and after resection with the knee prosthesis components.
Figure 10C:
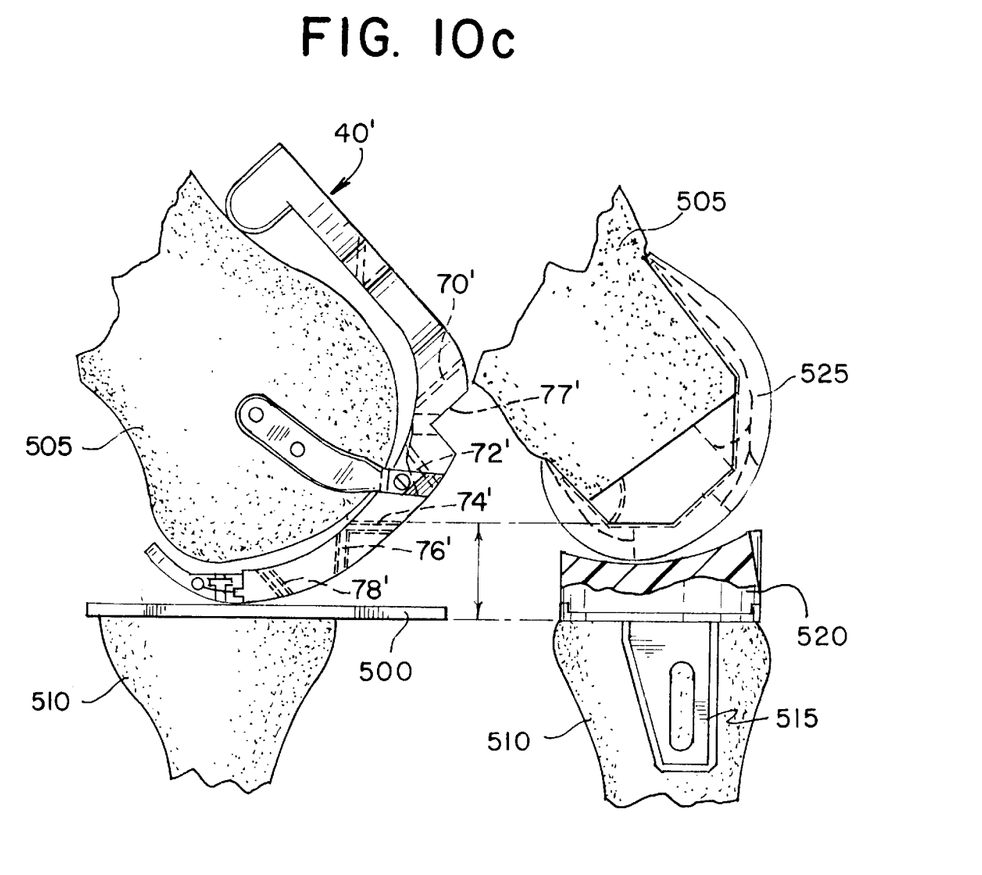
FIG. 10c is a side-by-side view of the 5-in-1 gap checking device at an angular position between full extension and 90 degrees flexion before resection of the distal end of the femur and after resection with the knee prosthesis components.

Once secured in its proper position, the gap checking device 40' is used to check the balance of the ligaments in extension, flexion and any position therebetween prior to making any cuts in the femur bone. If the ligaments are not properly balanced, the surgeon may perform selected releases of soft tissue (ligaments, capsule, muscle) to adjust the gaps in the conventional manner, while the gap checking device is still attached to the femur. In order to be able to check the balance of the ligaments, the thickness of the curved base 42' and shim 500, which protects the tibia bone, should be such that the patient's femur and tibia will be separated by the same distance that they will be separated after the femoral and tibial components of the knee prosthesis are in place. FIGS. 10a through 10c show side-by-side views of the gap checking device 40' and prosthesis components in full extension, 90 degrees flexion, and at an angle between full extension and 90 degrees flexion, respectively. FIG. 10a shows the femur bone 505, tibia bone 510 and prosthesis components including femoral component 525, tibial insert 520 and tibial tray 515. The distance denoted between the arrows is the same when the gap checking device 40' is properly positioned on the distal end of the femur prior to resection (left hand side of FIG. 10a) as it is after resection when the prosthesis components are put in place (right hand side of FIG. 10a). In other words, the distance from the slot 70' (used to make the distal cut in the femur bone) at the distal surface of the base 42' to the surface of the cut tibia bone is the same as the distance from the surface of the distal cut of the femur bone to the surface of the cut tibia when the prosthesis components are in place. To accommodate different thicknesses of tibial inserts, matching shims of different thicknesses are provided. The base 42' of the gap checking device 40' is therefore configured so that the balance of the ligaments may be checked over a continuous range-of-motion while the gap checking device 40' is secured to the distal end of the femur and prior to making cuts in the femur bone. This is advantageous over conventional techniques in which the cutting guide must first be removed and the prosthesis components placed on the cut femur and tibia in order to check the balance of the ligaments. The kinematics of the knee, while the gap checking device is secured to the femur and prior to making any cuts, will be substantially the same as the kinematics after the femoral and tibial components have been implanted, because the structure and outer surface of the gap checking device 40' is matched to the design of the prosthesis components. This way, balancing of the ligaments may be checked with the gap checking device while it is secured to the femur and before making any cuts to the femur, as if the femoral component itself was being tested.

Figure 5:
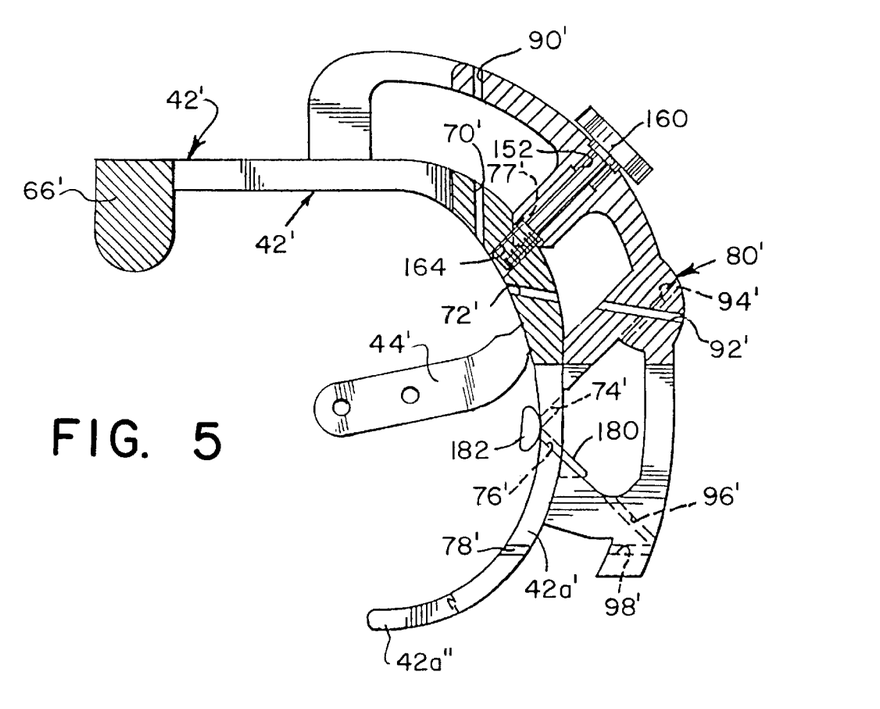
FIG. 5 is a partial cross-sectional side plan view of the assembled gap checking device and slot extender of FIG. 1.

After the gaps have been checked and the ligaments balanced, a slot extender 80' (FIG. 1) may be secured, if necessary, to the gap checking device 40' to lengthen the slots therein. To retain the gap checking device 40' and slot extender 80' together during the shaping operation, a thumb screw 150 is inserted through a hole 152 within the slot extender 80' and into engagement with a threaded bore 154 on the gap checking device 40'. As shown in FIG. 5, slot extender 80' includes slots 90', 92', 94', 96' and 98', aligned with the corresponding slots 70', 72', 74', 76' and 78' of the gap checking device 40', thereby lengthening or extending the slots through which a cutting blade can be inserted to shape the femur. The distal cut is made through slots 70' and 90'. The posterior cut is made through slots 78' and 98', and the anterior cut through slots 72' and 92'. The anterior chamfer cut is made through slots 76' and 96', and the posterior chamfer cut is made through slots 74' and 94'. It should be noted that the slot extender 80' is only used when the base is not sufficiently thick so that it is necessary to extend the length of the slot.

Figure 2:
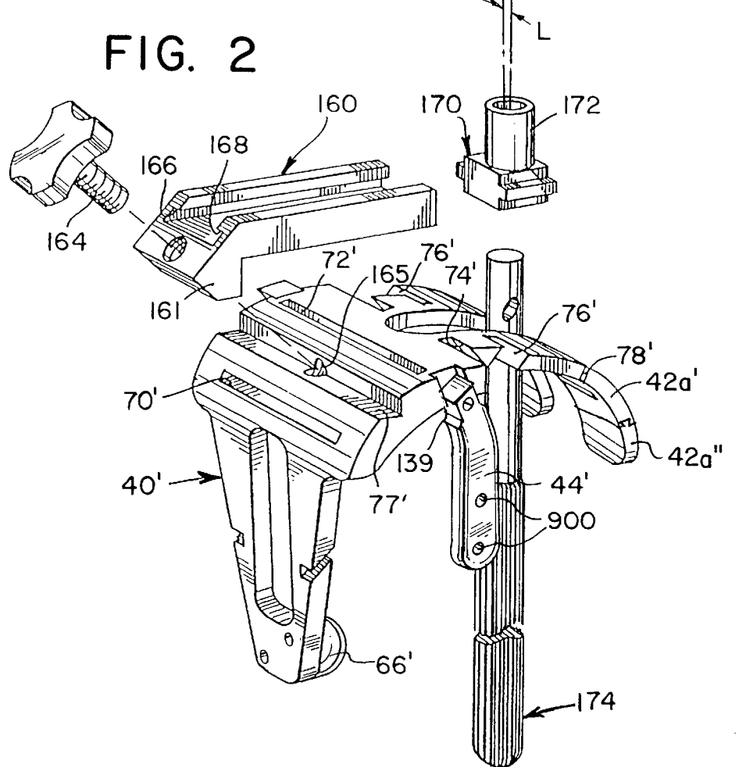
FIG. 2 is an exploded perspective view of a first embodiment of a gap checking device and intramedullary locating device in accordance with the present invention.
Figure 3:
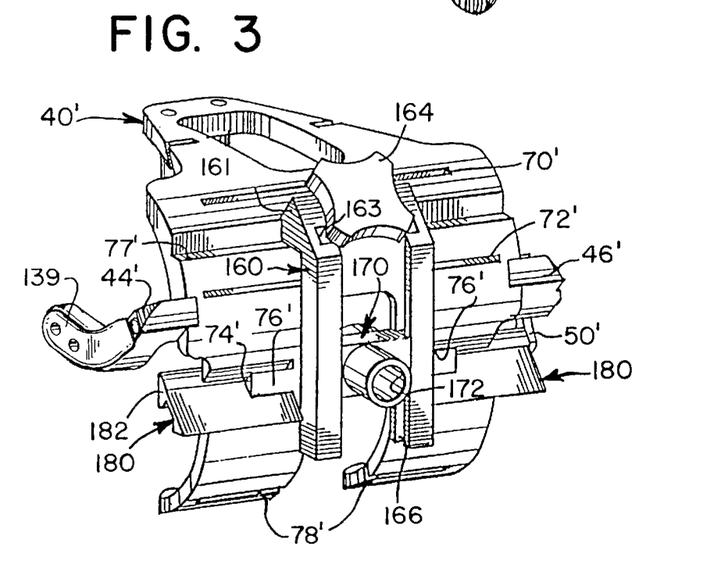
FIG. 3 is a perspective view from the front showing the assembled gap checking device and intramedullary locating device of FIG. 2.
Figure 4:
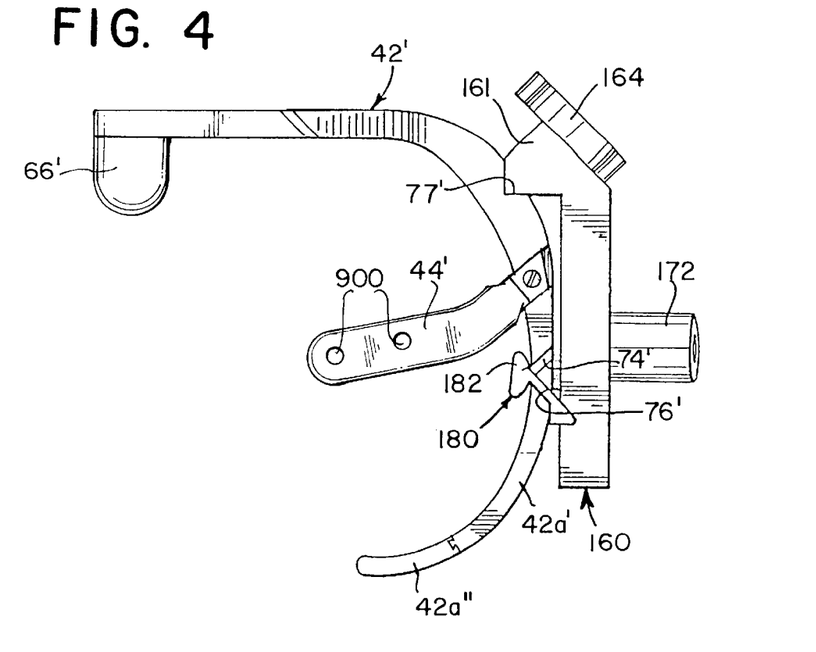
FIG. 4 is a side plan view of the assembled gap checking device and intramedullary locating device.

The operation of the intramedullary locating device and gap checking device 40' shown in FIGS. 1–6 is as follows. Initially, an intramedullary rod 174 is inserted into the intramedullary canal of the femur and then used to align the gap checking device. The intramedullary locating device used to provide intramedullary alignment, as shown in FIGS. 2–4, includes a first member 160 which has a triangular projection 161 that mates with the recess 77' of the gap checking device 40'. A first member 160 is secured to the gap checking device 40' by a screw 164 which engages a threaded hole 165 within the recess 77'. The first member 160 is shaped to form parallel tracks 166 and 168 in which a slider 170 having a base and an upstanding collar 172 projecting therefrom is displaceably positioned. The surgeon selects from among different upstanding collars 172 disposed at different angles a, relative to a reference axis perpendicular to the horizontal plane defined by the base in order to set the varus/valgus orientation angle. In a preferred embodiment, a is at an angle between approximately 2 degrees and approximately 7 degrees relative to a reference axis perpendicular to the horizontal plane defined by the base. The assembled intramedullary locating device and gap checking device 40' are placed on to the distal end of the femur so that the intramedullary rod 174 passes through the upstanding collar 172. Gap checking device 40' is properly positioned by: (1) displacing the gap checking device 40' along the axis of the intramedullary rod until the distal surface of the gap checking device 40' rests on the cartilage of the distal surface of the femur, (2) displacing the slider 170 within tracks 166, 168 of the first member 160 until the ball tip 66' rests on the anterior surface of the femur; and (3) rotating the gap checking device 40' until the free end of the outrigger arms 44', 46' are substantially aligned with the center of the medial and lateral epicondyles, respectively, of the femur.

If cartilage destruction is so significant that the outrigger arms 44', 46' do not align with the epicondyles of the knee when the distal surface of the gap checking device 40' rests on the cartilage of the femur, wedges 180 having the shape shown in FIGS. 3–5 may be used to fill in the space therebetween and ensure proper positioning of the gap checking device. Each wedge 180 includes a support surface 182 which is adapted to contact the distal surface of the femur when the gap checking device is properly positioned on the distal end of the femur. The wedges are preferably shaped so as to be supported in slots 76' of the gap checking device used to perform the anterior chamfer cut. Accordingly, the wedges 180 ensure the proper positioning of the gap checking device 40' so that the distal cut is accurately made in the femur.

Figure 6:
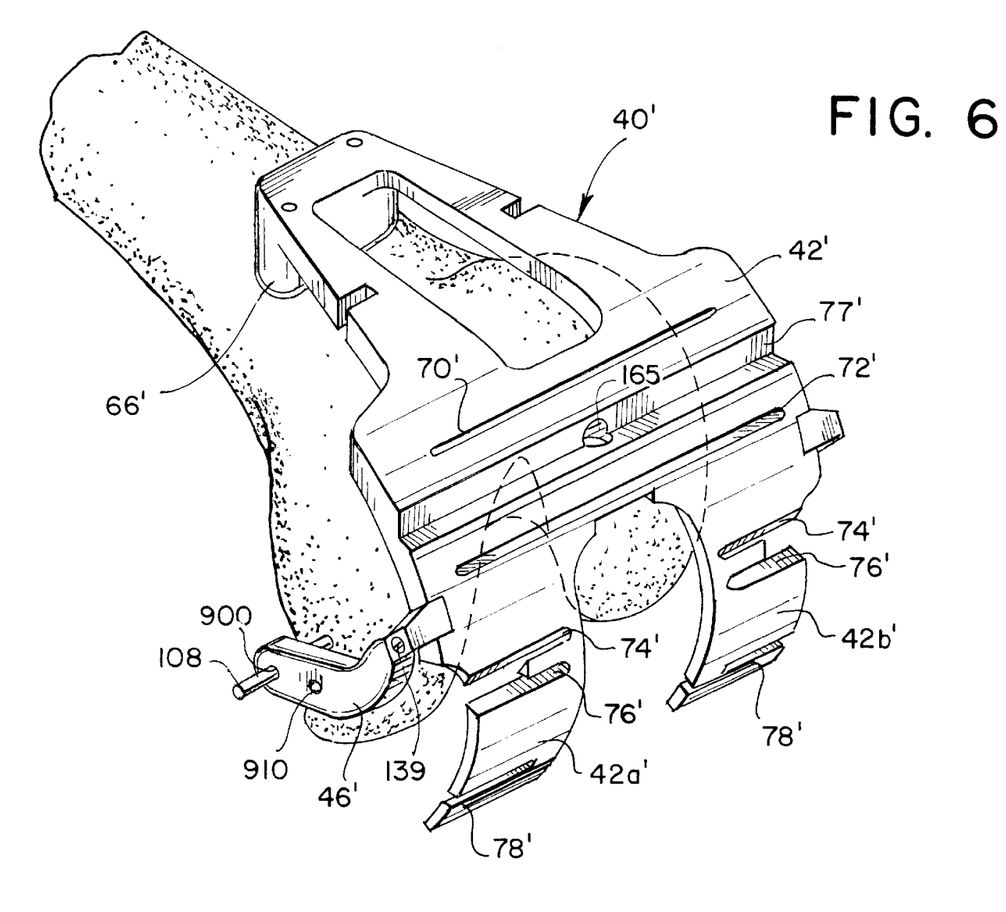
FIG. 6 is a perspective view of the gap checking device of FIG. 1 positioned on the femur bone after the locating device has been removed.
Figure 7A:
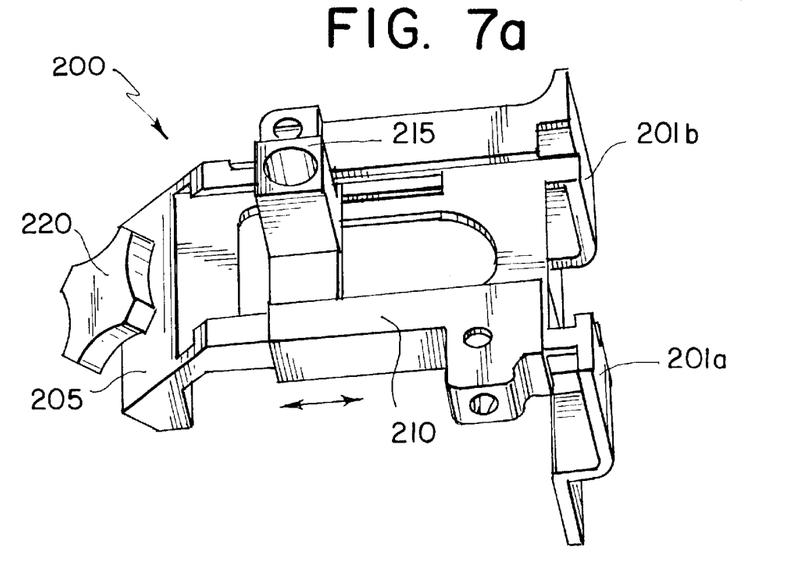
FIGS. 7a through 7d are different views of an alternative embodiment of the intramedullary locating device in accordance with the present invention.
Figure 7B:
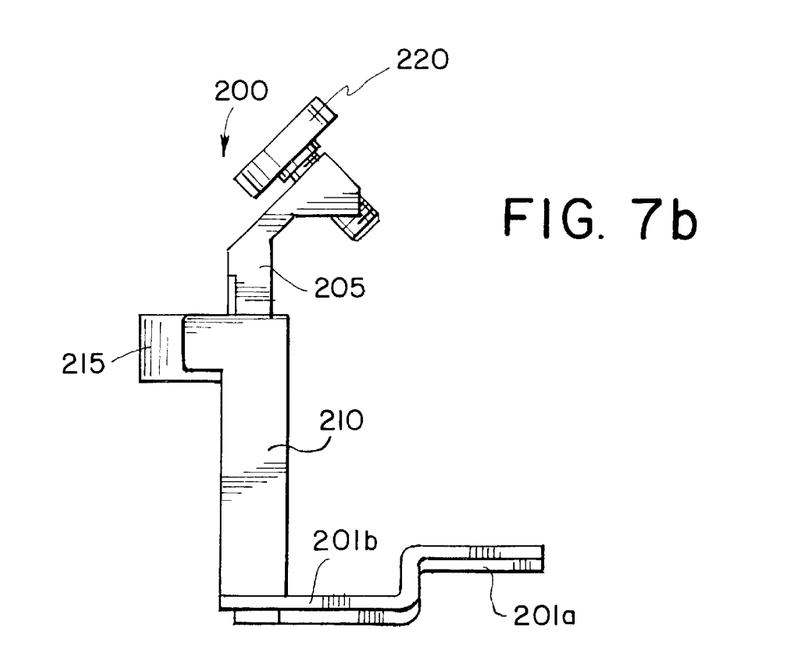
Figure 7C:
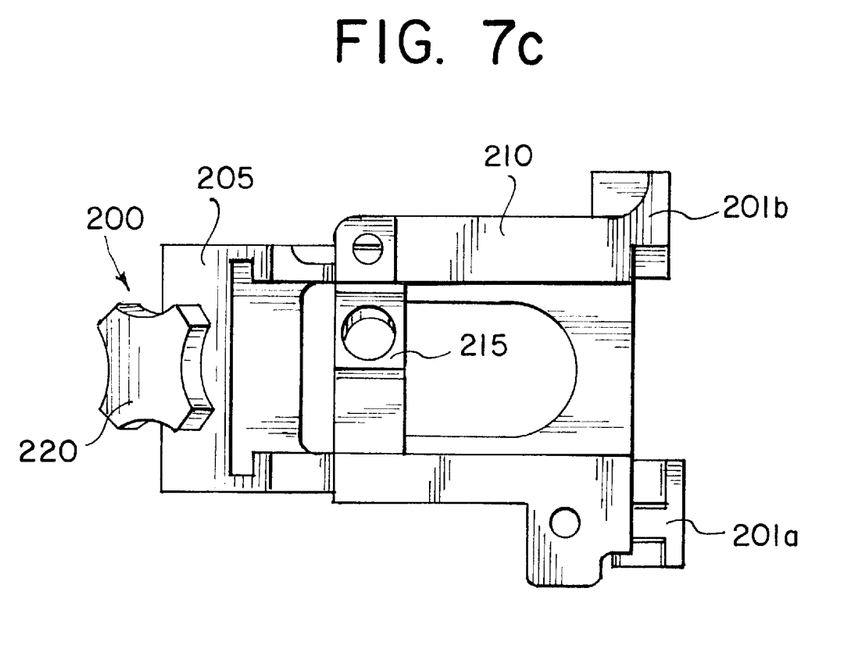
Figure 7D:
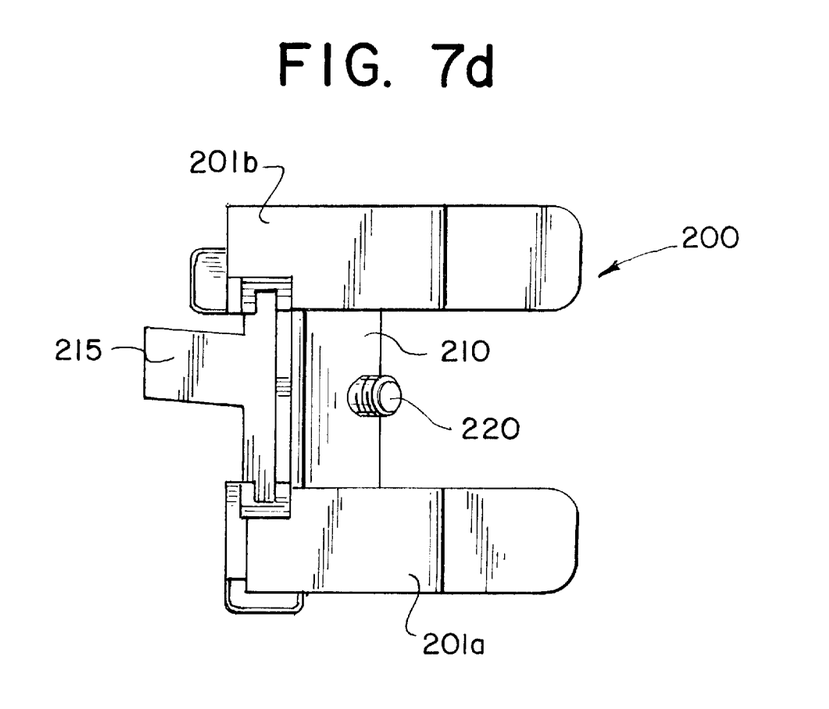

After the gap checking device 40' has been properly positioned on the femur, the surgeon tamps the pins 108 through apertures 900, 910 into the epicondyles and the anterior surface of the femur, respectively. Once secured in its proper position, the surgeon removes the intramedullary locating device and rod from the femur, as shown in FIG. 6. The gap checking device 40' is used to check the balance of the ligaments in full extension, approximately 45 degrees flexion, and any position therebetween. If the ligaments are not properly balanced, the surgeon may perform selected releases of soft tissue (ligaments, capsule, muscle) to adjust the gaps. If angle extenders 42a", 42b" are attached to the gap checking device 40' the balance of the ligaments in extension and flexion may be checked over a wider angular range from full extension to approximately 90 degrees flexion, and any position therebetween. The length of the slots of the gap checking device 40' may be extended by attaching the slot extender 80' to the gap checking device 40' via the thumb screw 150 received in the threaded apertures 152 and 154. The cutting instrument is then passed through the slots of the gap checking device and the slot extender 80' in order to make the cuts in the femur bone.

An alternative embodiment of an intramedullary locating device 200 in accordance with the present invention is shown in FIGS. 7a through 7d. Intramedullary locating device 200 includes a first member 205. A second member 210, having a channel defined therein and slidably displaceable in the direction indicated by the arrows so that the first member 205, is received in the channel of the second member and secured by a fastener 225. First member 205 is secured to the gap checking device 40' by a thumb screw 220 received in the threaded aperture 154. Slider 216 having a base 217 and an upstanding collar 215 slides within a track of the first member 205. In a preferred embodiment, the surgeon selects from among several available sliders each with the upstanding collar 215 disposed relative to a reference axis perpendicular to the horizontal plane defined by the base 217 at different fixed angles α, preferably at an angle between approximately 2 degrees and approximately 7 degrees, in order to set the varus/valgus orientation angle. It is within the intended scope of the invention to set the angle α, as desired. A free end of the second member 210 terminates in a movable paddle 201a and a fixed paddle 201b.

Figure 8A:
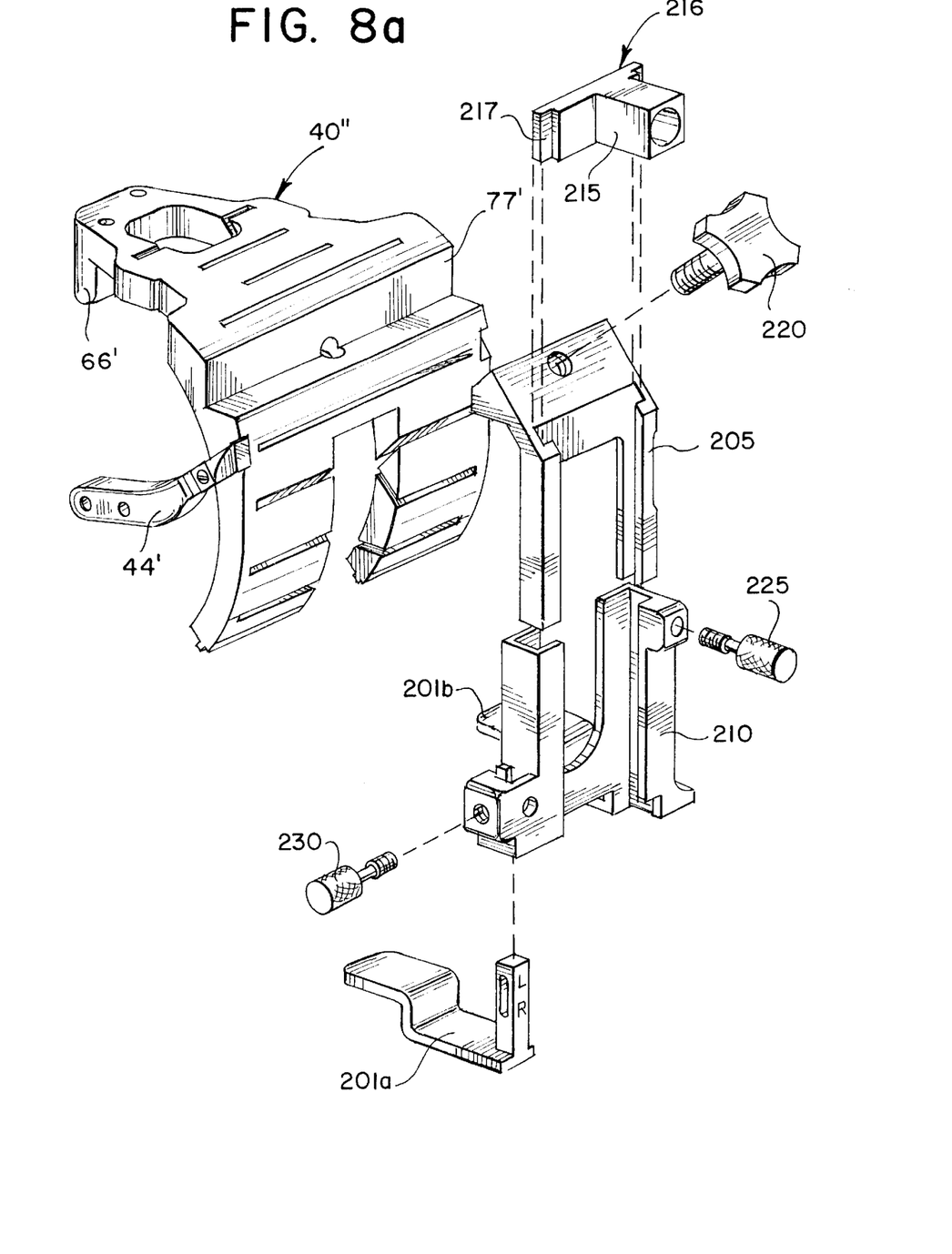
FIG. 8a is an exploded view of the alternative intramedullary locating device and an 8-in-1 gap checking device in accordance with the present invention.
Figure 8B:
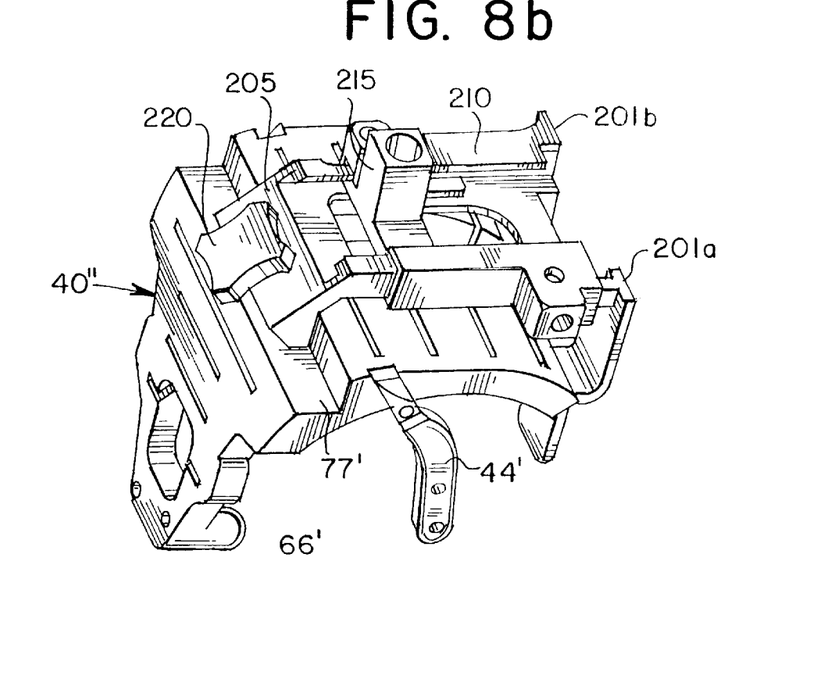
FIGS. 8b through 8d are different views of the alternative embodiment of the intramedullary locating device of FIGS. 8a assembled to the 8-in-1 gap checking device.
Figure 8C:
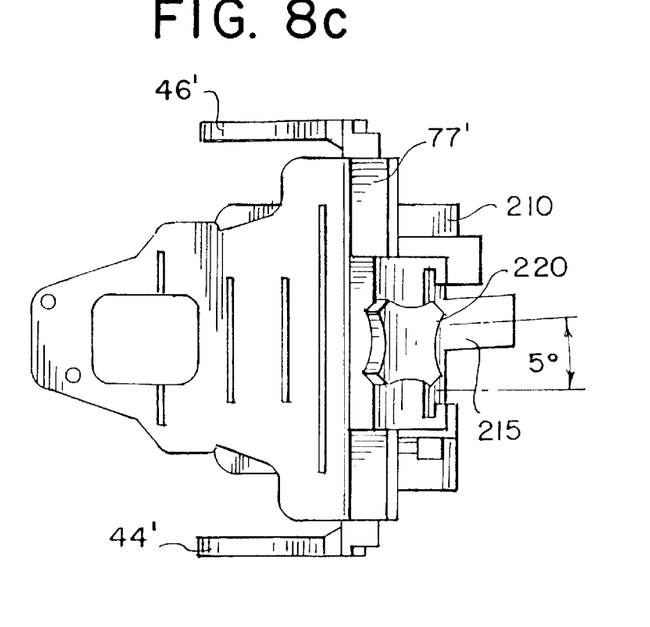
Figure 8D:
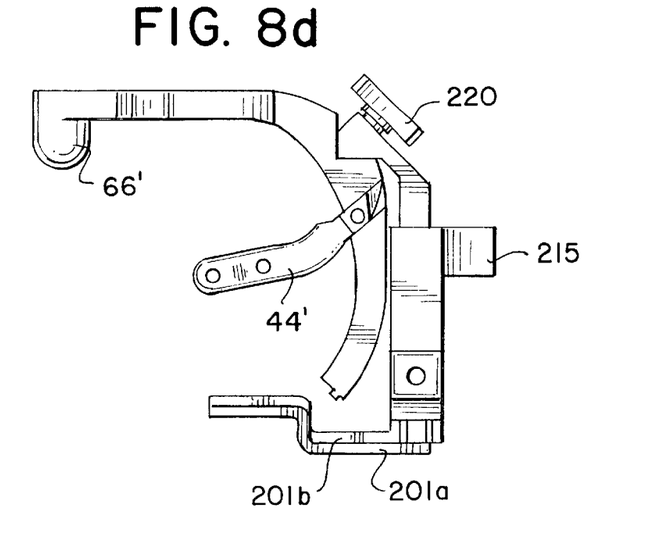
Figure 12:
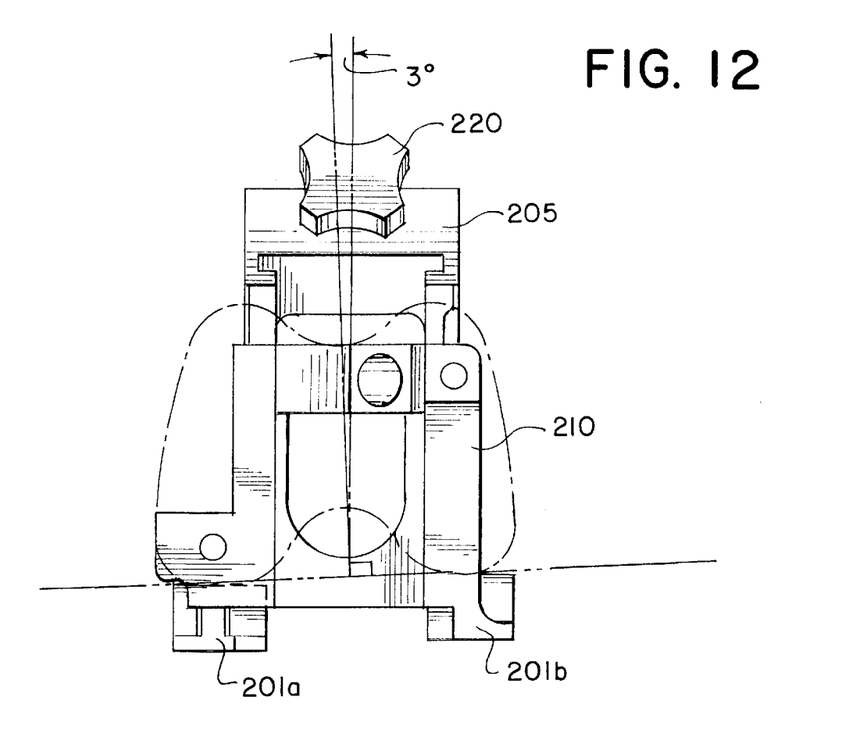
FIG. 12 is bottom view of the intramedullary locating device of FIGS. 7a–7d oriented at an angle of 3 degrees in a clockwise direction.

FIGS. 8a–8d show different embodiments of the alternative intramedullary locating device of FIGS. 7a–7d assembled to an alternative 8-in-1 gap checking device. In a preferred embodiment shown in FIG. 8a, movable paddle 201a is positionable in one of two predetermined settings (denoted "R" and "L"), preferably set to approximately 3 degrees rotation in a clockwise direction or approximately 3 degrees rotation in a counterclockwise direction, to account for external rotation of the femoral component relative to the femur for the right versus the left knee. Movable paddle 201a is secured in place by a fastener 230. By way of example, FIG. 12 shows the movable paddle 201a positioned such that the locating device 200 is offset 3 degrees in a clockwise direction relative to the reference plane denoted by the solid line. It should be noted, however, that the predetermined angular settings may be specified as desired. FIGS. 8b through 8d show the intramedullary locating device 200 assembled to the 8-in-1 gap checking device 40".

Figure 9A:
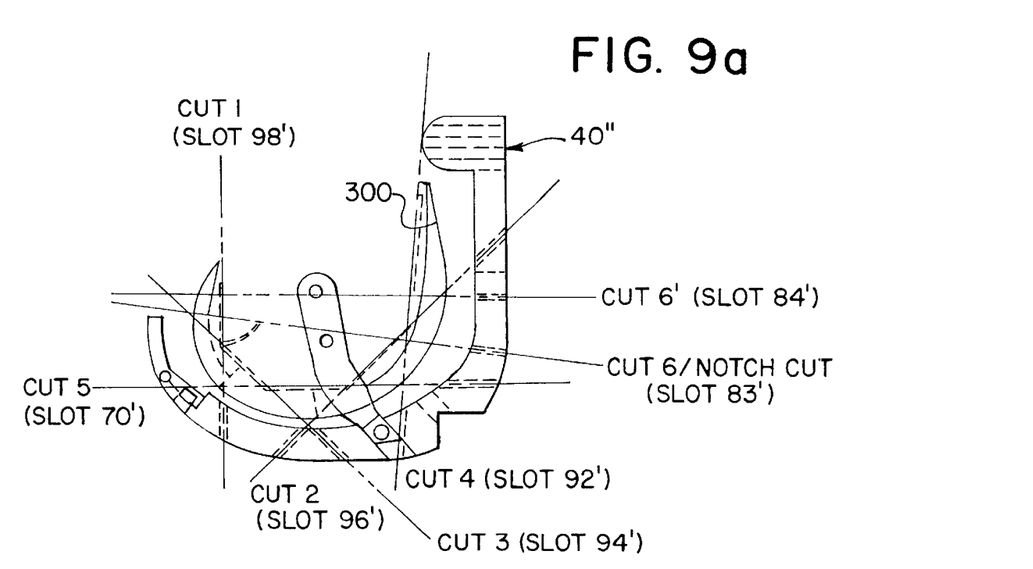
FIG. 9a is a side view of a femoral component and the 8-in-1 gap checking device in accordance with the present invention.
Figure 9B:
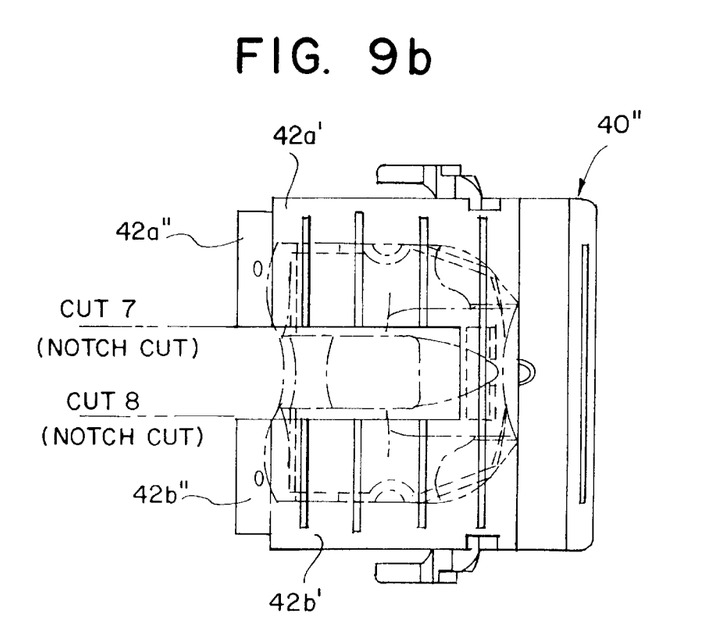

The features and details of the 8-in-1 gap checking device 40" are the same as those described above with respect to the first embodiment, except for additional slots forming cuts 6 through 8. FIGS. 9a and 9b show the 8-in-1 gap checking device 40" and the femoral component 300 of the knee prosthesis. The solid lines represent the cuts made in the distal end of the femur bone by passing the cutting blade or instrument through each of the slots defined in the gap checking device 40". The shape of the distal surface of the resected femur complements the distal surface of the femoral component 300. Cuts 1 through 5 shown in FIG. 9a correspond to slots 98', 96', 94', 92', 90', respectively, in FIG. 5. An additional three cuts 6, 7 and 8, are made in order to form a U-shaped notch in the distal end of the femur. Cuts 7 and 8 are parallel to one another and defined by the confronting surfaces of the bifurcated portions 42a', 42b'of the base 42', as shown in FIG. 9b. Cut 6 connects cuts 7 and 8 to form a U-shaped notch in the femur. In one embodiment slot 83' is used to form cut 6. In another embodiment, slot 84' may be used to form an alternate 6' cut to connect cuts 7 and 8, that is deeper than that formed using slot 83'. This alternative slot is suitable, for example, during revision when using a constrained condylar component. Although a single gap checking device 40" having both slots 83' and 84' is shown in FIGS. 8a–9b, since only one slot is used to form the 6th cut, it is also contemplated and within the intended scope of the invention to use two gap checking devices 40", one having slot 83' and the other having slot 84', from which the surgeon selects one.

In operation an intramedullary rod is inserted into the intramedullary canal of the femur bone. Movable paddle 201a is set to one of the predetermined positions depending on whether the left or right knee is being worked on. The intramedullary locating device 200 is secured to the gap checking device 40' via the thumb screw 220 and the assembled device is placed on to the distal end of the femur so that the intramedullary rod passes through the collar 215. Then the surgeon positions the gap checking device 40' by (1) displacing the gap checking device 40' along the axis of the intramedullary rod until the distal surface of the gap checking device 40' rests on the cartilage of the distal surface of the femur; (2) displacing the slider 215 within the tracks of the first member 205 until the ball tip 66' rests on the anterior surface of the femur; and (3) displacing the second member 210 relative to the first member 205 and rotating the gap checking device 40' until the paddles 201a, 201b contact the posterior condyles of the femur. As in the first embodiment, if necessary, a wedge may be inserted in slot 76' if the distal surface of the gap checking device 40' does not contact the distal end of the femur. Once the gap checking device 40' is properly aligned it is secured to the femur using pins 108 inserted through apertures 900, 910 and then the intramedullary locating device 200 is removed from the femur. A slot extender 80' may be attached to the gap checking device 40', as described in detail above with respect to the first embodiment.

Although the drawings and accompanying description only discuss an intramedullary locating technique, the gap checking device in accordance with the present invention is also suitable for extramedullary locating techniques.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed:

1. A method of shaping a femur preparatory to implanting a knee prosthesis having respective femoral and tibial components, said method comprising the steps of:
    applying a gap checking device to the distal end of the femur prior to resection, the thickness of the device corresponding in a predetermined way to the thickness of said femoral and tibial components;
    checking the gap; and
    shaping the distal end of the femur for the purpose of receiving the femoral component of said knee prosthesis after the gap has been checked.

2. A method according to claim 1, wherein said gap checking device is referenced to epicondyles of the knee.

3. A method according to claim 1, wherein said shaping step comprises passing a cutting device through slots in said gap checking device.

4. A method according to claim 3, further comprising the step of fastening a slot extender to said gap checking device.

5. A method according to claim 4, wherein said shaping step comprises passing a cutting device through slots in said gap checking device and said slot extender.

6. A gap checking device for checking ligament balance prior to resection of a femur and use in shaping the distal end of the femur preparatory to implantation of a knee prosthesis which includes femoral and tibial components, comprising:
    a curved base adapted to extend from the anterior of the femur around the distal end to the posterior of the femur and receive the distal end of the femur prior to resection.

7. A gap checking device according to claim 6, wherein said base is adapted so as to check ligament balance in any position of flexion and extension, while secured to the distal end of the femur.

8. A gap checking device according to claim 6, wherein said base is adapted so as to check ligament balance in at least three positions of flexion, while secured to the distal end of the femur.

9. A gap checking device according to claim 6, wherein said base has at least one slot defined therein through which a cutting device can be passed therethrough to form at least one resect in the distal end of the femur.

10. A gap checking device for checking ligament balance prior to resection of a femur and use in shaping the distal end of a femur preparatory to implantation of femoral and tibial components of a knee prosthesis, comprising:
    a curved base adapted to extend from the anterior of the femur around the distal end to the posterior of the femur and receive the distal end of the femur prior to resection; and
    a shim disposed proximate an outer surface of said base, said base and shim having a combined predetermined thickness so that when said base is secured to the distal end of the femur the gap separating the femur and tibia is maintained substantially equal to the separation when the femoral and tibial components are implanted.

11. A gap checking device for use in shaping the distal end of a femur preparatory to implantation of femoral and tibial components of a knee prosthesis, comprising:
    a curved base adapted to receive the distal end of the femur prior to resection, said base having at least one slot defined in said base and adapted so that a cutting device can be passed therethrough to form a distal cut in the femur; and a shim disposed proximate an outer surface of said base, said base and shim having a combined predetermined thickness so that when secured to the distal end of the femur the gap separating the femur and tibia is maintained substantially equal to the separation when the femoral and tibial components are implanted.

12. A method of shaping a femur preparatory to implanting a knee prosthesis having respective femoral and tibial components, said method comprising the steps of:

applying a gap checking device to the distal end of the femur prior to resection;

checking the gap; and shaping the distal end of said femur so as to receive the femoral component of said knee prosthesis after the gap has been checked.

13. A gap checking device for use in shaping the distal end of a femur preparatory to implantation of a knee prosthesis including femoral and tibial components, comprising:

a base having a curved inner surface adapted to fit around an uncut distal end of the femur and a curved outer surface being adapted so that when said base is connected to the femur, kinematics of the knee are substantially the same as kinematics of the implanted femoral and tibial components so as to check balancing of ligaments while said base is secured to said femur prior to resection of said femur.

14. A gap checking device in accordance with claim 13, wherein the kinematics of the knee and the kinematics of the implanted femoral and tibial components are substantially the same from full extension to approximately 90 degrees flexion.

15. A gap checking device in accordance with claim 13, wherein the kinematics of the knee and the kinematics of the implanted femoral and tibial components are substantially the same from full extension to approximately 45 degrees flexion.

16. An intramedullary locating device, comprising:

a first member having a track defined therein;

a slider having a base and an aperture defined therein, said slider being displaceable within the track of said first member;

an intramedullary rod adapted to be received through the aperture beyond the base and into the intramedullary canal of the femur; and a fixed paddle and a movable paddle, said paddles being disposed at a free end of said second member.

17. An intramedullary locating device in accordance with claim 16, wherein said base further comprises an upstanding collar projecting from said base through which said intramedullary rod is received.

18. An intramedullary locating device in accordance with claim 16, further comprising a second member having a track defined therein, said first member being slidably displaceable in the track of said second member.

19. An intramedullary locating device in accordance with claim 17, wherein said moveable paddle is oriented in one of two predetermined positions.

20. An intramedullary locating device in accordance with claim 19, wherein said two predetermined positions are set to account for external rotation of a femoral component relative to a femur for right and left knees.

21. An intramedullary locating device in accordance with claim 20, wherein said upstanding collar is disposed at an angle between approximately 2 degrees and approximately 7 degrees relative to a reference axis perpendicular to a plane defined by said base.

22. A method for intramedullary alignment of a gap checking device, comprising the steps of:

inserting an intramedullary rod into an intramedullary canal of a femur bone;

applying an assembled gap checking device and intramedullary locating device to a distal end of the femur, said intramedullary locating device including a first member having a track defined therein, and a slider having a base and an upstanding collar projecting therefrom;

passing said intramedullary rod through said upstanding collar of said intramedullary locating device; and displacing said slider within the track of said first member until said gap checking device is properly positioned on the distal end of the femur.

23. A method in accordance with claim 21, said intramedullary locating device further comprising a second member with a track defined therein and two paddles, one of which is movable.

24. A method in accordance with claim 23, wherein said applying step further comprises the step of adjusting a position of one of two paddles to account for external rotation of a femoral component relative to the femur for a right versus a left knee.

25. A method in accordance with claim 24, wherein said applying step further comprises the step of displacing said first member within the track of said second member until said paddles contact posterior condyles of the femur.

26. A method in accordance with claim 24, further comprising adjusting an angular orientation of said upstanding collar relative to a plane defined by said base so as to set a varus/valgus orientation angle.

27. An assembly for use in shaping the distal end of a femur preparatory to implantation of a knee prosthesis which includes femoral and tibial components, comprising:

a gap checking device having a curved base adapted to receive the distal end of the femur prior to resection and secured thereto for checking ligament balance prior to resection of the femur; and an intramedullary locating device, comprising:

a first member having a track defined therein;

a slider having a base and an aperture defined therein said slider being displaceable within the track of said first member; and an intramedullary rod adapted to be received in the aperture of the base.

28. An assembly in accordance with claim 27, wherein said slider has an upstanding collar projecting from the base adapted to received said intramedullary rod.

29. An assembly for use in shaping the distal end of a femur preparatory to implantation of a knee prosthesis which includes femoral and tibial components, comprising:

a gap checking device having a base adapted to receive the distal end of a femur prior to resection and check ligament balance prior to resection of the femur; and an intramedullary locating device, comprising:

a first member having a track defined therein;

a slider having a base and an aperture defined therein, said slider being displaceable within the track of said first member; and an intramedullary rod adapted to be received in the aperture of the base.

30. An assembly in accordance with claim 29, wherein said slider further comprises an upstanding collar projecting from the base and adapted to receive said intramedullary rod.

31. An assembly for use in shaping the distal end of a femur preparatory to implantation of a knee prosthesis, comprising:
 a gap checking device having a curved base adapted to receive the distal end of the femur prior to resection, said base having at least five slots defined therein; and
 an intramedullary locating device, comprising:
  a first member having a track defined therein;
  a slider having a base and an aperture defined therein, said slider being displaceable within the track of said first member; and
  an intramedullary rod adapted to be received in the aperture of the base.

32. An assembly in accordance with claim 31, wherein said slider further comprises an upstanding collar projecting from the base and adapted to receive said intramedullary rod.

33. An assembly for use in shaping the distal end of a femur preparatory to implantation of a knee prosthesis including femoral and tibial components, comprising:
 a gap checking device including a base having a curved inner surface adapted to fit around an uncut distal end of the femur and a curved outer surface being adapted so that when said base is connected to the femur, kinematics of the knee are substantially the same as kinematics of the implanted femoral and tibial components so as to check balancing of ligaments while said base is secured to said femur prior to resection of said femur; and
 an intramedullary locating device, comprising:
  a first member having a track defined therein;
  a slider having a base and an aperture defined therein, said slider being displaceable within the track of said first member; and
  an intramedullary rod adapted to be received in the aperture of the base.

34. An assembly in accordance with claim 33, wherein the kinematics of the knee and the kinematics of the implanted femoral and tibial components are substantially the same from full extension to approximately 90 degrees flexion.

35. An assembly in accordance with claim 33, wherein the kinematics of the knee and the kinematics of the implanted femoral and tibial components are substantially the same from full extension to approximately 45 degrees flexion.

36. An assembly in accordance with claim 33, wherein said slider further comprises an upstanding collar projection from the base and adapted to receive said intramedullary rod.

* * * * *